United States Patent [19]

Suyama et al.

[11] Patent Number: 5,075,495

[45] Date of Patent: Dec. 24, 1991

[54] 1-PHENYLCYCLOHEXYLPEROXY NEOALKANOATES AND USE THEREOF

[75] Inventors: Shuji Suyama; Tomoyuki Nakamura; Yasushi Sugihara, all of Chita, Japan

[73] Assignee: Nippon Oil and Fats Company, Limited, Tokyo, Japan

[21] Appl. No.: 530,785

[22] Filed: May 30, 1990

[30] Foreign Application Priority Data

Jun. 23, 1989 [JP] Japan ................................ 1-159679

[51] Int. Cl.[5] .................. C07C 331/00; C07C 409/00

[52] U.S. Cl. .................................................. 560/302

[58] Field of Search ........................................ 560/302

[56] References Cited

U.S. PATENT DOCUMENTS 3,796,757 3/1974 Chang ................................ 560/302

*Primary Examiner*—Mary C. Lee

*Assistant Examiner*—Robert C. Whittenbaugh

*Attorney, Agent, or Firm*—Stevens, Davis, Miller & Mosher

[57] ABSTRACT

A novel peroxy ester represented by the general formula (I):

(I)

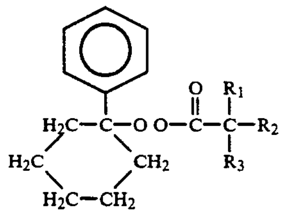

is useful as a polymerization initiator for vinyl chloride monomer.

1 Claim, No Drawings

1-PHENYLCYCLOHEXYLPEROXY NEOALKANOATES AND USE THEREOF

BACKGROUND OF THE INVENTION

1. Field of the Invention

This invention relates to novel 1-phenylcyclohexylperoxy neoalkanoates as a peroxyester and a use thereof as a polymerization initiator for vinyl monomers, particularly vinyl chloride.

2. Related Art Statement

In general, it is known that the peroxyesters can be used as a polymerization initiator for vinyl monomers, which is disclosed, for example, in Japanese Patent Application Publication No. 51-38752 and the like.

In the polymer industry, however, it is desired to increase the productivity of polymers from a viewpoint of economic reasons. Further, it is strongly demanded to develop a more active polymerization initiator for shortening the reaction time and increasing the production volume. The invention is to satisfy such a demand.

Moreover, a more active radical polymerization initiator is desirable to be used for objects other than the above production improvement. That is, such an object is concerned with the production of polyvinyl chlorides having a high polymerization degree.

In general, polyvinyl chlorides having a polymerization degree of not less than 1500 are called as a high polymerization degree product and are known to be particularly excellent in the properties such as mechanical strength, heat stability, dimensional stability, cold resistance and the like. Furthermore, when flexible polyvinyl chlorides are produced by adding a plasticizer to the polyvinyl chloride, rubbery elasticity can be enhanced as the polymerization degree becomes high.

As shown in the following Table 1, the polymerization degree of the polyvinyl chloride is determined by the polymerization temperature, so that in order to obtain a polyvinyl chloride having a high polymerization degree, vinyl chloride should be polymerized at a relatively low temperature of not higher than 50° C. From this reason, it is desired to develop a polymerization initiator having a sufficient activity even at a low temperature.

TABLE 1

| Polymerization temperature (°C.) | Polymerization degree |
|---|---|
| 62 | 800 |
| 57 | 1000 |
| 52 | 1300 |
| 50 | 1500 |
| 45 | 1900 |
| 40 | 2400 |
| 35 | 3000 |

It has hitherto been known to use diisobutyryl peroxide (hereinafter abbreviated as IBPO, Japanese Patent laid open No. 54-11190), acetylcyclohexylsulfonyl peroxide (hereinafter abbreviated as ACSP, Japanese Patent Application Publication No. 40-16795) or the like as a polymerization initiator having an activity even at the above low temperature when polymerizing vinyl chloride monomer.

And also, there is known a compound wherein α-carbon of carboxylic acid in peroxyester of cumylhydroperoxide is tertiary, such as cumylperoxy neodecanoate (hereinafter abbreviated as CND, Japanese Patent laid open No. 58-120611) or the like.

However, there are some problems in the polymerization methods using IBPO, ACSP and CND as a polymerization initiator. That is, IBPO is very unstable against water and is decomposed by contacting with water, so that the polymerization activity is not held and hence the yield of the polymer is low. On the other hand, ACSP has a problem in view of the hygiene of decomposition products and is poor in the heat stability because the resulting polymer is colored. Furthermore, CND produces a peculiar odor in the polymer because of the decomposition products based on the cumylperoxy group.

In the field of peroxides, it is well-known that a half-valued period of a peroxide (measure on the activity of the peroxide) is remarkably changed by varying the structure of the peroxide.

That is, in case of peroxy esters, the activity can be changed by the structure variation of carboxylic group and hydroperoxy group.

The peroxy esters obtained by the conventional technique and having an activity at a lowest temperature are compounds in which hydroperoxide is cumyl hydroperoxide.

These compounds are active at a low temperature as compared with peroxy esters derived from the other t-alkyl hydroperoxides such as t-butyl hydroperoxide, t-amyl hydroperoxide, t-octyl hydroperoxide or the like when the carboxyalkyl group is same.

That is, a temperature requiring that a half-valued period of 0.1 mol/l of t-butylperoxy neodecanoate (hereinafter abbreviated as BND), t-amylperoxy neodecanoate or t-octylperoxy neodecanoate (hereinafter abbreviated as OND) in benzene is 10 hours (hereinafter referred to as 10 hour halflife temperature) is 41°-47° C., while the 10 hour halflife temperature of CND is as low as 37° C. As previously mentioned, however, there are problems in the polymerization method using CND, so that it is further demanded to develop a polymerization initiator having an activity at a lower temperature in order to conduct low temperature polymerization for the shortening of polymerization time and the increase of production volume.

SUMMARY OF THE INVENTION

The inventors have made various studies over a long time for solving the above problems of the conventional techniques and confirmed that a novel compound not reported in an article, i.e. 1-phenylcyclohexylperoxy neoalkanoate is short in the half-valued period as compared with the conventionally used peroxy esters and further is high in the activity in the polymerization of vinyl chloride and is useful as an initiator for providing polymers having good properties, and as a result the invention has been accomplished.

That is, the invention is concerned with 1-phenylcyclohexylperoxy neoalkanoate represented by the following general formula (I):

(I)

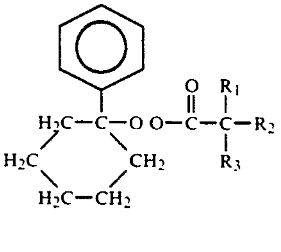

(wherein $R_1$, $R_2$ and $R_3$ are alkyl group having a carbon number of 1-9, respectively, provided that the carbon number in total of $R_1$, $R_2$ and $R_3$ is 3-11).

Furthermore, the invention relates to a use of such a peroxy ester in polymerization of vinyl monomers. That is, the invention lies in a method of polymerizing vinyl chloride, characterized in that a particular peroxy ester represented by the above general formula (I) is used as a polymerization initiator alone or together with at least one polymerization initiator selected from peroxy diester, diacyl peroxide and peroxy dicarbonate having a temperature of 30°-65° C. requiring that a half-valued period of 0.1 mol/l concentration in benzene is 10 hours in the homopolymerization of vinyl chloride monomer or copolymerization of vinyl chloride monomer and a monomer copolymerizable therewith.

Moreover, the upper limit of the carbon number in $R_1$-$R_3$ of the general formula (I) is determined by considering the practical utility.

DESCRIPTION OF THE PREFERRED EMBODIMENTS

As a concrete example of the peroxy ester according to the invention, there are 1-phenylcyclohexylperoxy pivalate, 1-phenylcyclohexylperoxy neohexanoate, 1-phenylcyclohexylperoxy neononanoate, 1-phenylcyclohexylperoxy neodecanoate, 1-phenylcyclohexylperoxy neotridecanoate and the like.

The peroxy esters according to the invention can be obtained, for example, according to the conventional manner as follows.

That is, they are obtained by reacting a chloride of a carboxylic acid with 1-phenylcyclohexyl hydroperoxide in the presence of sodium hydroxide, potassium hydroxide or an amine such as pyridine or the like as a catalyst under the same reaction conditions as in the conventional peroxy ester production.

In this case, they can be synthesized in a solvent such as aromatic hydrocarbon (e.g. toluene, ethylbenzene), aliphatic hydrocarbon (e.g. pentane, hexane, octane, petroleum naphtha, mineral spirit) or aliphatic hydrocarbon consisting essentially of isoparaffin (e.g. Shellzole, trade name, made by Shell Chemical Co., Ltd.), or diluted therewith after the synthesis. Moreover, the reaction temperature is about $-10°$ C. to $+30°$ C.

The chloride of carboxylic acid used in the invention can be produced by reacting a carboxylic acid with a chlorinating agent such as $PCl_3$, $POCl_3$, $SOCl_2$ or the like and isolating an acid chloride from the resulting reaction product.

As the carboxylic acid used in the invention, mention may be made of pivalic acid, neoheptanoic acid, neooctanoic acid, neononanoic acid, neodecanoic acid, neotridecanoic acid (the last five acids are an isomer mixture of carboxylic acids having a total carbon number of 7, 8, 9, 10, 13 among carboxylic acids generally called as "neoacid" in which α-carbon atom of carboxylic acid is completely substituted with an alkyl group) and the like.

1-Phenylcyclohexyl hydroperoxide used in the invention is produced by air oxidation of phenylcyclohexane, or may be produced by treating 1-phenylcyclohexanol with an excessive amount of hydrogen peroxide in the presence of a strong acid catalyst such as sulfuric acid, phosphoric acid, perchloric acid or acid body of ion exchanging resin, or p-toluene sulfonic acid.

As another vinyl monomer copolymerizable with vinyl chloride monomer used in the invention, mention zation rate tends to be slow. While, when it exceeds 1 may be made of ethylene, vinyl acetate, vinylidene chloride, styrene, acrylic ester and so on.

The polymerization initiator used in the invention is 1-phenylcyclohexylperoxy neoalkanoate represented by the general formula (I). The amount of the initiator added is 0.001-1 part by weight, preferably 0.01-0.5 part by weight as a pure product based on 100 parts by weight of vinyl chloride monomer charged. When the amount is less than 0.001 part by weight, the polymeripart by weight, it is difficult to control polymerization reaction and the properties of the resulting polymer are undesirably degraded.

Furthermore, a polymerization initiator used together with the polymerization initiator according to the invention is at least one of peroxy ester, diacyl peroxide and peroxy dicarbonate having a 10 hour halflife temperature of 30°-65° C.

Concretely, the peroxy ester includes t-butylperoxy pivalate (55° C.), BND (46.5° C.), OND (40.7° C.), CND (36.6° C.) and so on, and the diacyl peroxide includes IBPO (32.5° C.), 3,5,5-trimethylhexanoyl peroxide (59.5° C.), lauroyl peroxide, (62° C.), octanoyl peroxide (62° C.) and so on, and the peroxy dicarbonate includes di(2-ethoxyethyl) peroxy dicarbonate (hereinafter abbreviated as OPP, 43.4° C.), di-n-propylperoxy dicarbonate (40.5° C.), diisopropylperoxy dicarbonate (40.5° C.) and so on.

The amount of the latter polymerization initiator added is properly selected, but it is usually ¼ to 4 times that of 1-phenylcyclohexylperoxy neoalkanoate.

The polymerization method used in the invention is usually suspension polymerization. In this case, there is caused no problem in the usual compounding recipe except for the use of the polymerization initiator according to the invention.

The polymerization temperature is generally 10°-75° C., preferably 30°-60° C. When the polymerization temperature is lower than 10° C., the polymerization tends to take a long time, while when it exceeds 75° C., the life of the polymerization initiator becomes short and it is difficult to attain a high polymerization degree through polymerization.

1-Phenylcyclohexylperoxy neoalkanoates according to the invention represented by the general formula (I) are novel compounds and have a characteristic that the decomposition halflife period is shorter than that of the conventionally known peroxy ester. Therefore, the polymerization rate can be increased by using the peroxy ester according to the invention alone or together with the conventional particular initiator as a polymerization initiator in the conventional polymerization. Thus, the polymerization cycle time can be shortened and the production volume can be increased. At the same time, the resulting polymer has no odor and a good heat stability, particularly no coloring. Furthermore, the polymerization of vinyl chloride at a lower temperature can be made by using the peroxy ester according to the invention, whereby polyvinyl chloride having a high polymerization degree and excellent properties can be obtained.

The following examples are given in illustration of the invention and are not intended as limitations thereof.

EXAMPLE 1

Synthesis of 1-phenylcyclohexylperoxy neodecanoate

In a four-necked flask of 200 ml provided with a stirrer was charged 33.7 g of an aqueous solution of 30% potassium hydroxide, to which was added a mixture of 22.1 g of 95% 1-phenylcyclohexyl hydroperoxide and 30 g of benzene while the liquid temperature was maintained at 10° C. with stirring. Furthermore, 19.1 g of neodecanoyl chloride was added dropwise over 7 minutes while the liquid temperature was maintained at 15° C. with stirring. After the liquid temperature was raised to 25° C. and the stirring was continued for 2 hours, 40 g of cold water was added and further the stirring was made for 5 minutes. The water phase was separated and washed with an aqueous solution of 40 g of 5% sodium hydroxide and further with water three times. The solution was dried on magnesium sulfate anhydride and benzene was removed off under vacuum to obtain 24.0 g of a desired compound as a light yellow liquid. This compound had an active oxygen amount of 4.20%, a purity of 91% through calculation and a yield of 63 mol %.

The identification of this compound was confirmed by IR and NMR spectra. The results are shown in Table 2.

EXAMPLE 2

Synthesis of 1-phenylcyclohexylperoxy pivalate

The same synthesis as in Example 1 was repeated, except that pivalic chloride was used as a chloride of carboxylic acid, to obtain a desired compound as a colorless liquid. The identification of this compound was confirmed by IR and NMR spectra. The results are shown in Table 2.

EXAMPLE 3

Synthesis of 1-phenylcyclohexylperoxy neohexanoate

The same synthesis as in Example 1 was repeated, except that neohexanoyl chloride was used as a chloride of carboxylic acid, to obtain a desired compound as a colorless liquid. The identification of this compound was confirmed by IR and NMR spectra. The results are shown in Table 2.

EXAMPLE 4

Synthesis of 1-phenylcyclohexylperoxy neononanoate

The same synthesis as in Example 1 was repeated, except that neononanoyl chloride obtained by chlorination of neononanic acid (aliphatic fatty acid made by Idemitsu Petrochemical Co., Ltd.: Equacid 9, trade name) was used as a chloride of carboxylic acid, to obtain a desired compound as a colorless liquid. The results are shown in Table 2.

EXAMPLE 5

Synthesis of 1-phenylcyclohexylperoxy neotridecanoate

The same synthesis as in Example 1 was repeated, except that neotridecanoyl chloride obtained by chlorination of neotridecanoic acid (aliphatic fatty acid made by Idemitsu Petrochemical Co., Ltd.: Equacid 13, trade name) was used as a chloride of carboxylic acid, to obtain a desired compound as a colorless liquid. The results are shown in Table 2.

TABLE 2

| Example | Structural formula | Active oxygen amount (%) | Purity (%) | Yield (%) | IR $\nu_{C=O}$(cm$^{-1}$) | $^1$H NMR(CDCL$_3$) |
|---|---|---|---|---|---|---|
| 1 | 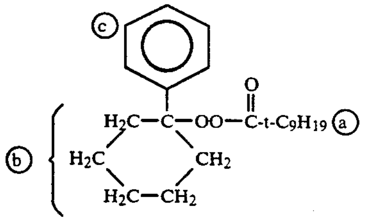 | 4.20 | 91 | 63 | 1770 | H(a) : δ0.63~1.54, m, 19H<br>H(b) : δ1.30~2.15, m, 10H<br>H(c) : δ7.23~7.52, m, 5H |
| 2 | 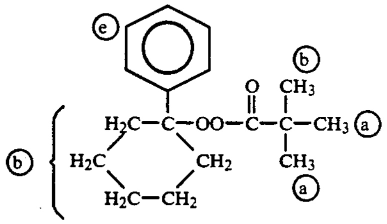 | 5.37 | 93 | 71 | 1765 | H(a) : δ0.97, s, 9H<br>H(b) : δ1.23~2.15, m, 10H<br>H(c) : δ7.24~7.49, m, 5H |
| 3 | 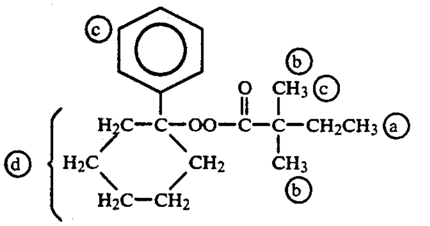 | 5.10 | 93 | 66 | 1766 | H(a) : δ0.69, t, 3H<br>H(b) : δ1.00, s, 6H<br>H(c) : δ1.41, q, 2H<br>H(d) : δ1.22~2.15, m, 10H<br>H(e) : δ7.20~7.51, m, 5H |

TABLE 2-continued

| Example | Structural formula | Active oxygen amount (%) | Purity (%) | Yield (%) | IR $\nu_{c=o}$(cm$^{-1}$) | $^1$H NMR(CDCL$_3$) |
|---|---|---|---|---|---|---|
| 4 | 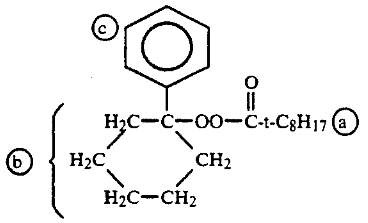 | 4.53 | 94 | 62 | 1765 | H(a) : δ0.67 ~ 1.55, m, 17H<br>H(b) : δ1.22 ~ 2.16, m, 10H<br>H(c) : δ7.22 ~ 7.50, m, 5H |
| 5 | 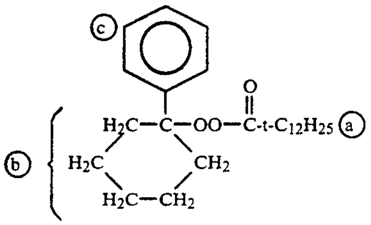 | 3.70 | 90 | 59 | 1765 | H(a) : δ0.65 ~ 1.60, m, 25H<br>H(b) : δ1.24 ~ 2.15, m, 10H<br>H(c) : δ7.23 ~ 7.49, m, 5H |

EXAMPLE 6

The heat decomposition test was made in benzene as a solvent with respect to the peroxy esters according to the invention produced in Examples 1 to 5 (concentration: 0.1 mol/l) to measure 10 hour halflife temperature. For the comparison, the 10 hour halflife temperature ($T_{10}$) of the known cumylperoxy ester was measured in the similar manner. The results are shown in Table 3.

It is apparent from these results that the decomposition halflife time of 1-phenylcyclohexylperoxy neoalkanoates according to the invention are shorter than that of the conventional known cumylperoxy esters.

TABLE 3

| Peroxy esters | $T_{10}$ (°C.) |
|---|---|
| peroxy neodecanoate | |
| 1-phenylcyclohexyl | 30.9 |
| cumyl | 36.6 |
| octyl | 40.7 |
| butyl | 46.5 |
| peroxy pivalate | |
| 1-phenylcyclohexyl | 39.1 |
| cumyl | 45.2 |
| peroxy neohexanoate | |
| 1-phenylcyclohexyl | 35.1 |
| cumyl | 41.0 |
| peroxy neononanoate | |
| 1-phenylcyclohexyl | 30.1 |
| cumyl | 35.9 |
| peroxy neotridecanoate | |
| 1-phenylcyclohexyl | 30.5 |
| cumyl | 36.1 |

$T_{10}$: 10 hour halflife temperature (in benzene, 0.1M)

Polymerization of Vinyl Chloride

EXAMPLE 7

Into a stainless autoclave of 400 ml capacity were charged 200 ml of ion exchanged water and 0.1 part by weight of polyvinyl alcohol. After 1-phenylcyclohexylperoxy neodecanoate (hereinafter abbreviated as PCHND) obtained in Example 1 was added in an amount of 0.07 part by weight as a pure product, the resulting mixture was cooled below −80° C. and mixed with 100 parts by weight of vinyl chloride monomer. After a space portion of the autoclave was fully substituted with nitrogen gas, the autoclave was closely sealed. It was immersed in a thermostatic water chamber held at 45° C. for 8 hours to conduct polymerization. In this case, the stirring was made by rotating the autoclave in the water chamber at 32 r.p.m. After the polymerization and the cooling, the unreacted vinyl chloride monomer was removed and the resulting white powder was washed with 100 ml of water two times and dried under vacuum. The thus obtained vinyl chloride polymer had a yield of 83% from its weight and an average polymerization degree of 2020. The following coloring test for the heat stability of the vinyl chloride polymer was made and also the odor of the polymer was measured The results are shown in Table 4.

Coloring Test and Odor 100 parts by weight of vinyl chloride polymer was mixed with 50 parts by weight of dioctylphthalate and 2.5 parts by weight of dibutyl tin maleate and kneaded on rolls at 160° C. for 10 minutes, from which a sheet of 1 mm in thickness was taken out. The coloring degree of the sheet was visually observed. At the same time, the odor of the sheet was measured.

EXAMPLES 8, 9

The polymerization of vinyl chloride monomer was carried out in the same manner as in Example 7 except that the amount of PCHND added and the polymerization temperature were varied. The results are shown in Table 4.

EXAMPLE 10

The polymerization of vinyl chloride monomer was carried out in the same manner as in Example 7 except that 0.03 part by weight of PCHND and 0.03 part by weight of OND were used instead of 0.07 part by weight of PCHND as a polymerization initiator in Example 7. The results are shown in Table 4.

EXAMPLES 11, 12

The polymerization of vinyl chloride monomer was carried out in the same manner as in Example 7 except that 0.03 part by weight of PCHND and 0.03 part by weight of OPP or IBPO instead of OND were used as a polymerization initiator in Example 10. The results are shown in Table 4.

EXAMPLE 13

The polymerization was carried out in the same manner as in Example 7 except that 90 parts by weight of vinyl chloride monomer and 10 parts by weight of vinyl acetate monomer were used instead of 100 parts by weight of vinyl chloride monomer in Example 7 and the polymerization temperature was 50° C. The results are shown in Table 4.

COMPARATIVE EXAMPLE 1

The polymerization of vinyl chloride monomer was carried out in the same manner as in Example 7 except that 0.07 part by weight of IBPO was used instead of 0.07 part by weight of PCHND as a polymerization initiator in Example 7. The results are shown in Table 4.

COMPARATIVE EXAMPLES 2, 3

The polymerization of vinyl chloride monomer was carried out in the same manner as in Example 7 except that 0.07 part by weight of ACSP or CND was used instead of 0.07 part by weight of PCHND as a polymerization initiator in Example 7. The results are shown in Table 4.

COMPARATIVE EXAMPLE 4

The polymerization of vinyl chloride monomer was carried out in the same manner as in Example 10 except that 0.03 part by weight of CND was used instead of 0.03 part by weight of PCHND together with 0.03 part by weight of OND as a polymerization initiator in Example 10. The results are shown in Table 4.

As seen from Table 4, the polymers having good properties are obtained in a good yield by the method using the polymerization initiator according to the invention as compared with the use of the conventional polymerization initiator.

TABLE 4

| | Example | | | | | | | Comparative Example | | | |
|---|---|---|---|---|---|---|---|---|---|---|---|
| | 7 | 6 | 9 | 10 | 11 | 12 | 13 | 1 | 2 | 3 | 4 |
| Vinyl chloride monomer (part by weight) | 100 | 100 | 100 | 100 | 100 | 100 | 90 | 100 | 100 | 100 | 100 |
| Vinyl acetate monomer (part by weight) | 0 | 0 | 0 | 0 | 0 | 0 | 10 | 0 | 0 | 0 | 0 |
| Polymerization temperature (°C.) | 45 | 40 | 50 | 45 | 45 | 45 | 50 | 45 | 45 | 45 | 45 |
| Addition amount[1] | | | | | | | | | | | |
| PCHND | 0.07 | 0.10 | 0.04 | 0.03 | 0.03 | 0.03 | 0.07 | | | 0.07 | |
| OND | | | | 0.03 | | | | | | | 0.03 |
| OPP | | | | | 0.03 | | | | | | |
| IBPO | | | | | | 0.03 | | 0.07 | | | |
| ACSP | | | | | | | | | 0.07 | | |
| CND | | | | | | | | | | 0.07 | 0.03 |
| Yield (%)[2] | 83 | 84 | 83 | 87 | 85 | 82 | 76 | 75 | 77 | 78 | 80 |
| Average polymerization degree | 2020 | 2540 | 1490 | 2030 | 2010 | 2010 | — | 2030 | 2020 | 1990 | 2000 |
| Coloring | colorless | colorless | colorless | colorless | colorless | colorless | colorless | colorless | light red | colorless | colorless |
| Odor | absence | absence | absence | absence | absence | absence | absence | absence | absence | presence of slight odor[3] | absence |

Note
[1]converted into pure product (part by weight)
[2]polymerization time: 8 hours
[3]weak odor similar to acetophenone or phenol

EXAMPLE 14

The polymerization of vinyl chloride monomer was carried out in the same manner as in Example 7 except that 0.03 part by weight of 1-phenylcyclohexylperoxy pivalate (hereinafter abbreviated as PCHPV) obtained in Example 2 and 0.03 part by weight of BND were used instead of 0.07 part by weight of PCHND as a polymerization initiator in Example 7 and the polymerization temperature was 52° C. As a result, the yield of polyvinyl chloride was 84%.

COMPARATIVE EXAMPLE 5

The polymerization of vinyl chloride monomer was carried out in the same manner as in Example 14 except that 0.03 part by weight of cumylperoxy pivalate was used instead of 0.03 part by weight of PCHPV together with 0.03 part by weight of BND as a polymerization initiator in Example 14 for the comparison. As a result, the yield of polyvinyl chloride was 79%.

EXAMPLE 15

The polymerization of vinyl chloride monomer was carried out in the same manner as in Example 7 except that 0.03 part by weight of 1-phenylcyclohexylperoxy neohexanoate (hereinafter abbreviated as PCHNH) obtained in Example 3 and 0.03 part by weight of BND were used instead of 0.07 part by weight of PCHND as a polymerization initiator in Example 7 and the polymerization temperature was 50° C. As a result, the yield of polyvinyl chloride was 83%.

EXAMPLE 16

The polymerization of vinyl chloride monomer was carried out in the same manner as in Example 7 except that 0.07 part by weight of 1-phenylcyclohexylperoxy neononanoate (hereinafter abbreviated as PCHNN) obtained in Example 4 was used instead of 0.07 part by weight of PCHND as a polymerization initiator in Example 7 and the polymerization temperature was 45° C.

As a result, the yield of polyvinyl chloride was 85%. The obtained polymer had no odor and coloring.

COMPARATIVE EXAMPLE 6

The polymerization of vinyl chloride monomer was carried out in the same manner as in Example 15 except that 0.03 part by weight of cumylperoxy neononanoate was used instead of PCHNN as a polymerization initiator in Example 16 for the comparison As a result, the yield of polyvinyl chloride was 81%.

This polymer had a slight odor similar to acetophenone.

EXAMPLE 17

The polymerization of vinyl chloride monomer was carried out in the same manner as in Example 15 except that 0.03 part by weight of PCHNN and 0.03 part by weight of OPP were used instead of 0.07 part by weight of PCHNN as a polymerization initiator in Example 16 and the polymerization temperature was 45° C. As a result, the yield of polyvinyl chloride was 86%. The obtained polymer had no odor and coloring.

EXAMPLE 18

The polymerization of vinyl chloride monomer was carried out in the same manner as in Example 15 except that 0.03 part by weight of PCHNN and 0.03 part by weight of BND were used instead of 0.07 part by weight of PCHNN as a polymerization initiator in Example 16 and the polymerization temperature was 45° C. As a result, the yield of polyvinyl chloride was 85%. The obtained polymer had no odor and coloring.

What is claimed is:

1. 1-Phenylcyclohexylperoxy neoalkanoate represented by the following general formula (I):

(I)

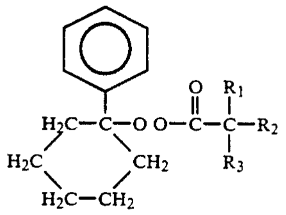

(wherein $R_1$, $R_2$ and $R_3$ are alkyl group having a carbon number of 1-9, respectively, provided that the carbon number in total of $R_1$, $R_2$ and $R_3$ is 3-11).

* * * * *